US00PP18183P3

(12) United States Plant Patent
Bridgen

(10) Patent No.: US PP18,183 P3
(45) Date of Patent: Nov. 6, 2007

(54) ***ALSTROEMERIA* PLANT NAMED 'MAUVE MAJESTY'**

(50) Latin Name: ***Alstroemeria* hybrid L.**
Varietal Denomination: Mauve Majesty

(75) Inventor: Mark P. Bridgen, Southold, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 11/339,765

(22) Filed: Jan. 25, 2006

(65) Prior Publication Data

US 2007/0174941 P1 Jul. 26, 2007

(51) Int. Cl.
*A01H 5/00* (2006.01)

(52) U.S. Cl. ..... Plt./309

(58) Field of Classification Search ..... Plt./309
See application file for complete search history.

*Primary Examiner*—Kent Bell
*Assistant Examiner*—June Hwu
(74) *Attorney, Agent, or Firm*—Jondle & Associates, P.C.

(57) ABSTRACT

An *Alstroemeria* cultivar particularly distinguished by its mauve flower color, its strong, upright flower stems, its winter hardiness, and its continuous flowering from beginning of summer until the first hard freeze in the fall is disclosed.

2 Drawing Sheets

Genus and species: *Alstroemeria* hybrid L.
Variety denomination: 'Mauve Majesty'.

BACKGROUND OF THE NEW PLANT

The present invention comprises a new and distinct cultivar of *Alstroemeria,* botanically known as *Alstroemeria* hybrid L., and hereinafter referred to by the cultivar name 'Mauve Majesty'. 'Mauve Majesty' originated from a hybridization made in 2002 in Riverhead, N.Y. The female parent was an *Alstroemeria aurea* plant (unpatented), while the male parent was the proprietary *Alstroemeria* plant 'Purple 1' (unpatented).

Fifteen days after pollination, embryos were aseptically removed in ovulo and cultured on a one-quarter strength Murashige and Skoog medium. When the embryos germinated in vitro, they were subcultured to full-strength Murashige and Skoog medium for continued development. Once they were large enough to remove from the culture vessel, they were acclimated and grown in the greenhouse for trial. A single plant selection was chosen for further evaluation and for asexual propagation in 2002 in Riverhead, N.Y.

'Mauve Majesty' was selected for its distinctive mauve flower color, continuous flowering, and strong, upright flower stems. It was also selected because it is winter hardy to temperatures as low as those experienced in USDA zone 5. 'Mauve Majesty' has been asexually propagated repeatedly by rhizome division and tissue culture since 2002 and has been found to retain its distinctive characteristics through successive asexual propagations.

DESCRIPTION OF PHOTOGRAPHS

This new *Alstroemeria* plant is illustrated by the accompanying photographs which show blooms and foliage of the plant; the colors shown are as true as can be reasonably obtained by conventional photographic procedures.

DESCRIPTION OF THE NEW CULTIVAR

Figure 1:
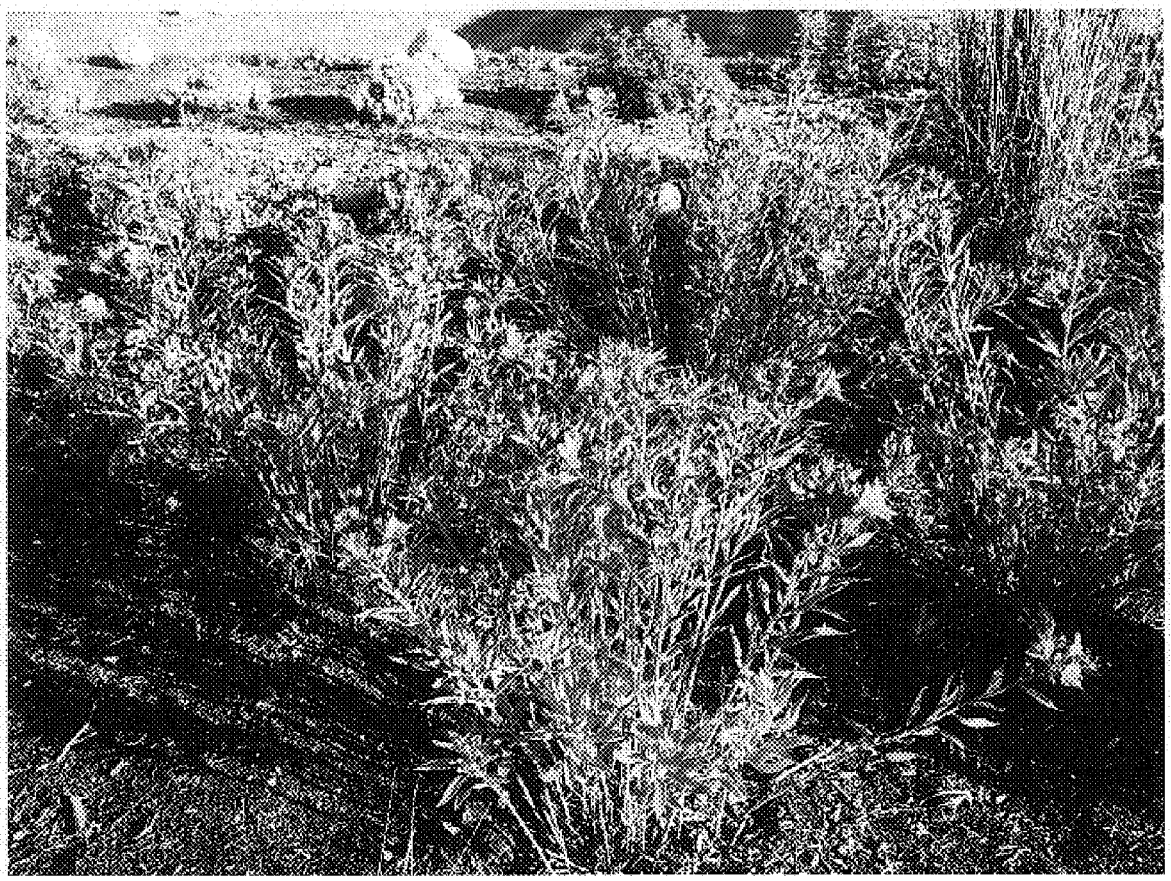
FIG. 1 shows the overall plant habit.
Figure 2:
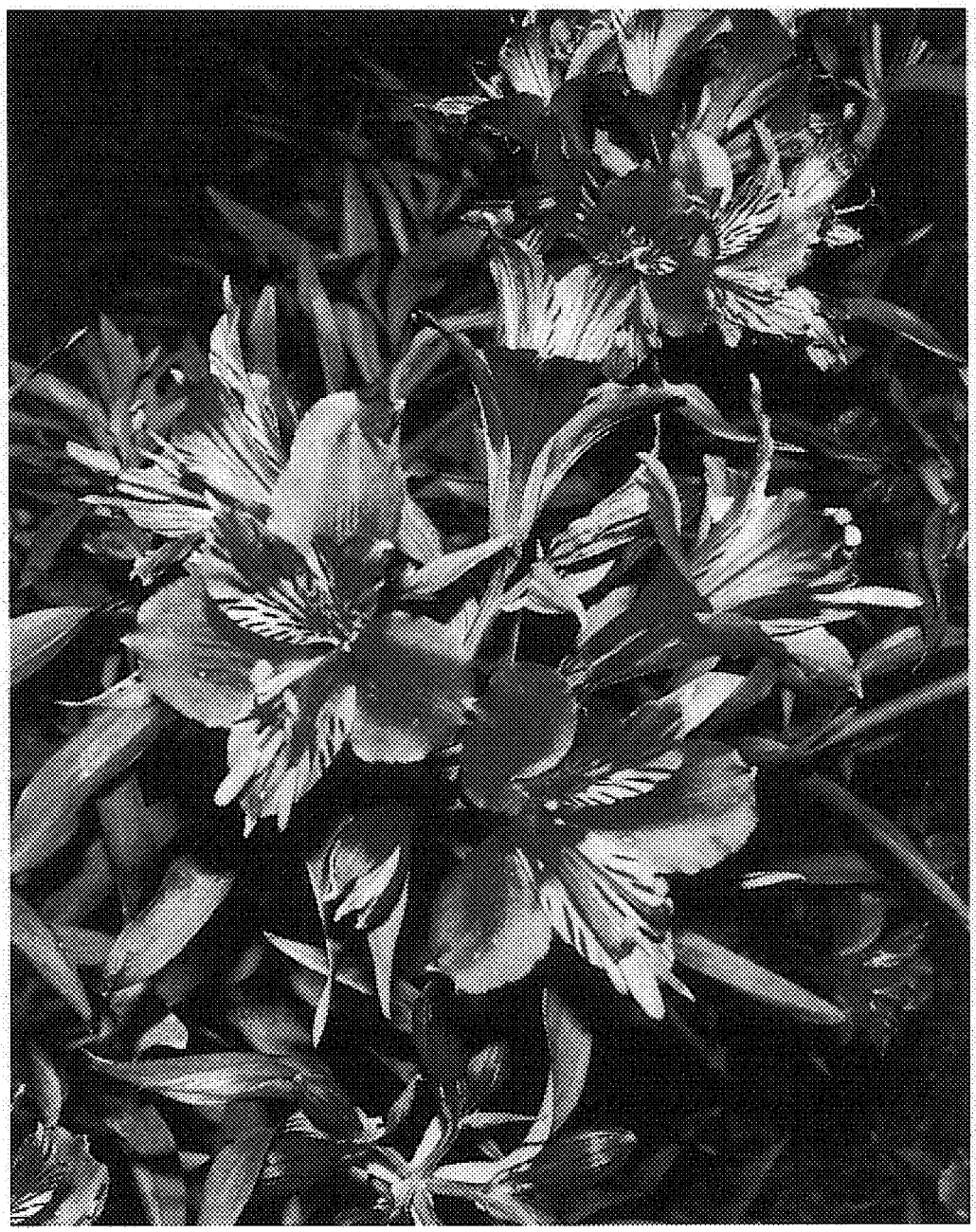
FIG. 2 shows mature inflorescences, flower buds, and leaves.

The following detailed descriptions set forth the distinctive characteristics of 'Mauve Majesty'. The data which define these characteristics were collected from asexual reproductions carried out in Riverhead, N.Y. The data were collected on plants grown under field conditions in full sun. Color references are primarily to The R.H.S. Colour Chart of The Royal Horticultural Society of London (R.H.S.).

DETAILED BOTANICAL DESCRIPTION

Classification:
- *Botanical.*—*Alstroemeria* hybrid L.
- *Common name.*—*Alstroemeria,* Lily-of-the-Incas; Inca Lily; Peruvian Lily.

Parentage:
- *Female parent.*—*Alstroemeria aurea* (unpatented).
- *Male parent.*—Proprietary *Alstroemeria* plant 'Purple 1' (unpatented).

Plant:
- *Origin.*—Seedling derived from ovule-cultured hybrid embryos.
- *Form.*—Herbaceous plant arising from an underground rhizome.
- *Habit.*—Upright and vigorous.
- *Plant size.*—Height: 75–80 cm. Width (Spread): 90–100 cm.
- *Flowering habit.*—Continuous from the beginning of summer until the first hard freeze in fall.
- *Time to bloom from propagation.*—If a clump is divided in the spring or early summer, it will resume flowering within a month.

Flowering stems:
*Color.*—RHS 137A or RHS 137C.
*Description.*—Long, strong, and upright growing floral stems.
*Size.*—Length: 62.5–80 cm. Diameter: 1–2 cm.
*Internode length.*—Not applicable.
*Texture.*—Glabrous.
*Color.*—RHS 137A (Dark green).
*Vegetative stem length.*—70–75 cm.

Leaves:
*Arrangement.*—Simple, linear, resupinate leaves with parallel venation that are arranged alternately.
*Shape.*—Elongated elliptic with extended bases.
*Apex.*—Broadly acuminate apices.
*Base.*—Extended.
*Margin.*—Entire.
*Color.*—Upper surface: RHS 137A or RHS 137C. Lower surface: RHS 137A or RHS 137C.
*Size.*—Length: 10 cm. Width: 2.2 cm.
*Texture.*—Glabrous leaf surface.
*Venation.*—Parallel.
*Pubescence.*—None.
*Petiole.*—None (sessile leaves).

Flowers:
*Inflorescence type.*—A terminal bracted umbel of cymes.
*Flowering season.*—Summer through early fall.
*Lastingness of individual flowers on the plant.*—15–21 days.
*Flower width.*—Approximately 5 cm at the open end.
*Flower depth.*—3.7–4.2 cm.
*Flower shape.*—Tubular.
*Fragrance.*—None.
*Number of flowers per plant.*—Everblooming; varies with size of plant; 30–50 flowers per plant over 3 months.
*Umbel.*—Length (height): 7.0 cm to 10.0 cm. Diameter: 11.0 cm to 15.0 cm.
*Number of florets per umbel.*—Typical: 15. Range: 10–20.
*Pedicel.*—Length: 0.02 cm to 0.10 cm. Strength: Strong. Texture: Glabrous. Color: RHS 71A to RHS N79C.

Peduncle:
*Length.*—2.5–4 cm.
*Diameter.*—Approximately 0.9–1 cm before opening.
*Texture.*—Glabrous.
*Color.*—RHS 188A; when the peduncle is touched, the outer covering rubs off to a color of about RHS N77D to RHS N77B.

Flower buds:
*Color.*—RHS 70B to RHS 71B.
*Shape.*—Pear-shaped becoming long and more pointed just before opening.
*Size.*—Length: Approximately 2.5 to 2.8 cm before opening. Diameter: Approximately 0.9 to 1 cm before opening.

Tepals:
*Arrangement.*—Two concentric circles of three tepals each.
*Shape.*—Tubular/spatulate to oblanceolate-spatulate.
*Size (for both the inner and outer tepals).*—Length: 3.5 cm to 5.5 cm. Width: 1.5 cm to 2.5 cm at the widest point.
*Apex.*—Emarginate to mucronate to apiculate apices.
*Texture.*—Glabrous.
*Color.*—Inner tepal, upper surface: At the very base of the inner tepal, the color is green fading to RHS 4D (pale yellow to yellow/green) and RHS 192D (green) with a spot of RHS N189B; the area of the base color is usually no longer than 1 cm. The color then progresses to the tip from RHS N80D, RHS 77B, RHS N81B and finally to RHS 77A at the tip. Throughout, there are dark, tiny stripes of RHS 53A. Inner tepal, lower surface: The lowest tip of the outside of the inner tepal is either RHS 4D (whitish-yellow) or darker, RHS 53A. The color progresses to the tip from RHS N80D (but lighter), RHS 77B (but lighter), RHS N81B (but lighter) and finally to RHS 77A (but lighter) at the tip. Throughout, there are dark, tiny stripes of RHS 53A (but lighter) (the colors mimic the upper surface of the tepal, and progress to the tip similar to those in the previous section but paler and less intense). Outer tepal, upper surface: RHS 71A on the perimeter and the lower part and intensifying to RHS N79C at the tip. The color progresses to the tip from RHS N80D (but darker), RHS 77B (but darker), RHS N81B (but darker) and finally to RHS 77A (but darker) at the tip. (the colors are similar to the upper surface of the inner tepal but darker in most cases). There are stripes of RHS 53A. Outer tepal, lower surface: RHS 71A, but darker on the perimeter and the lower part and intensifying to RHS N79C, but darker at the tip. The color progresses to the tip from RHS N80D, but darker, RHS 77B, but darker, RHS N81B, but darker (the colors are similar to the upper surface of the outer tepal). There are none to few stripes of RHS 53A. The tips and central parts are RHS 83A.

Reproductive organs:
*Pistils.*—Number: 1. Style length: 2.5–4.0 cm. Style color: RHS N57D. Stigma color: RHS N57D or lighter.
*Stamens.*—Number: 6.
*Filaments.*—Length: Approximately 2.5–4.0 cm. Filament color: RHS N57D. Anther color: RHS 166A to RHS 183A.
*Pollen.*—Flowers are sterile, therefore no pollen is produced.
*Seeds.*—None.

Disease and insect resistance: Because this plant is sterile, there is no pollen and thrips are less likely to attack.

COMPARISON WITH PARENTAL AND COMMERCIAL CULTIVARS

The female parent, *Alstroemeria aurea* (unpatented), is a species that is native to southern Chile and it differs from 'Mauve Majesty' by having yellow to orange flowers and by flowering only in the spring and early summer whereas 'Mauve Majesty' has mauve flowers and flowers continuously from the beginning of summer until the first hard freeze in fall.

The male parent, 'Purple 1' (unpatented), has larger flowers than 'Mauve Majesty' with a different shade of purple and is not as floriferous as 'Mauve Majesty'. In addition, 'Purple 1' is not hardy to USDA zone 5, whereas 'Mauve Majesty' is hardy to USDA zone 5.

'Mauve Majesty' differs from the commercial *Alstroemeria* cultivar 'Sweet Laura' (U.S. Plant Pat. No. 10,030), by having mauve flowers that lack fragrance, whereas 'Sweet Laura' has yellow flowers that are fragrant. Both cultivars are winter hardy to USDA zone 5.

I claim:

1. A new and distinct cultivar of *Alstroemeria* plant as described and shown herein.

* * * * *